US012733787B2

(12) United States Patent
Mannion et al.

(10) Patent No.: US 12,733,787 B2
(45) Date of Patent: Sep. 15, 2026

(54) ENDOSCOPE IMAGING SYSTEM

(71) Applicant: C. R. Bard, Inc., Franklin Lakes, NJ (US)

(72) Inventors: Paul Thomas Mannion, Eliot, ME (US); Padraig Fogarty, Ballina-Killaloe (IE); Tony Garvey, Listowel (IE)

(73) Assignee: C. R. Bard, Inc., Franklin Lakes, NJ (US)

(*) Notice: Subject to any disclaimer, the term of this patent is extended or adjusted under 35 U.S.C. 154(b) by 237 days.

(21) Appl. No.: 18/563,848

(22) PCT Filed: May 16, 2022

(86) PCT No.: PCT/US2022/029425
§ 371 (c)(1),
(2) Date: Nov. 22, 2023

(87) PCT Pub. No.: WO2022/250996
PCT Pub. Date: Dec. 1, 2022

(65) Prior Publication Data

US 2024/0225415 A1 Jul. 11, 2024

Related U.S. Application Data

(60) Provisional application No. 63/192,742, filed on May 25, 2021.

(51) Int. Cl.
*A61B 1/00* (2006.01)
*A61B 17/00* (2006.01)

(52) U.S. Cl.
CPC ........ *A61B 1/00009* (2013.01); *A61B 1/0004* (2022.02); *A61B 1/0005* (2013.01);
(Continued)

(58) Field of Classification Search
CPC . A61B 1/00009; A61B 1/0004; A61B 1/0005; A61B 2017/00154;
(Continued)

(56) References Cited

U.S. PATENT DOCUMENTS 10,471,159 B1 * 11/2019 Lapotko ............... A61K 49/221
11,147,636 B2 * 10/2021 Hallen ................ A61B 3/0025
(Continued)

FOREIGN PATENT DOCUMENTS

WO 2022250996 A1 12/2022

OTHER PUBLICATIONS

PCT/US2022/029425 filed May 16, 2022 International Search Report and Written Opinion dated Sep. 23, 2022.

*Primary Examiner* — Anh Tuan T Nguyen
*Assistant Examiner* — Shankar Raj Ghimire
(74) *Attorney, Agent, or Firm* — Rutan & Tucker LLP

(57) ABSTRACT

Disclosed herein is an endoscope imaging system including an endoscope configured to capture one or more images, the endoscope in communication with a laser system and a display, and a console, in communication with the endoscope, the laser system and the display, the console configured to receive one or more parameter settings from the laser system, receive the one or more captured images from the endoscope, generate one or more icons corresponding to the parameter settings and overlay the icons on the captured images depicted on the display.

19 Claims, 6 Drawing Sheets

(52) U.S. Cl.
CPC .... *A61B 17/00* (2013.01); *A61B 2017/00154* (2013.01); *A61B 2017/00199* (2013.01); *A61B 2017/00973* (2013.01)

(58) Field of Classification Search
CPC .... A61B 2017/00199; A61B 2034/258; A61B 2090/373; A61B 34/25
See application file for complete search history.

(56) References Cited

U.S. PATENT DOCUMENTS

| | | | | |
|---|---|---|---|---|
| 2002/0173778 | A1* | 11/2002 | Knopp | A61B 3/13 606/5 |
| 2003/0100824 | A1* | 5/2003 | Warren | B05C 5/0225 600/407 |
| 2009/0275929 | A1* | 11/2009 | Zickler | A61B 3/113 606/4 |
| 2011/0082450 | A1* | 4/2011 | Melsky | A61B 18/24 606/14 |
| 2015/0257830 | A1* | 9/2015 | Tyc | A61N 7/022 606/11 |
| 2015/0305604 | A1* | 10/2015 | Melsky | A61B 18/20 600/104 |
| 2017/0189108 | A1* | 7/2017 | Melsky | A61B 18/082 |
| 2017/0196453 | A1* | 7/2017 | Papac | A61B 3/10 |
| 2017/0215695 | A1* | 8/2017 | Harrah | A61B 1/00042 |
| 2019/0216540 | A1* | 7/2019 | Melsky | A61B 18/18 |
| 2020/0030044 | A1 | 1/2020 | Wang et al. | |
| 2020/0033584 | A1* | 1/2020 | Jeong | A61B 1/00096 |
| 2020/0402235 | A1 | 12/2020 | Shigeta et al. | |
| 2023/0401688 | A1* | 12/2023 | Mishina | G01N 29/06 |

* cited by examiner 150
122
120
110
100

FIG. 4
180B
RIGHT
Right Pedal
0.1J
200Hz
PW-S
20W
LEFT
Left Pedal
0.05J
400Hz
PW-M
20W
180A
150

ENDOSCOPE IMAGING SYSTEM

PRIORITY

This application is a U.S. national stage application of International Application No. PCT/US2022/029425, filed May 16, 2022, which claims the benefit of priority to U.S. Provisional Application No. 63/192,742, filed May 25, 2021, each of which is incorporated by reference in its entirety into this application.

BACKGROUND

During medical procedures that use a laser system and an endoscope, it can be difficult for a physician to view settings on the laser system while viewing the endoscope monitor. Often times, the physician must turn their head to look at the laser system for verifying the settings and then turn their head back to the endoscope monitor. It would be beneficial for the physician to be able to verify the laser settings direction on the endoscope monitor. Disclosed herein is a system and method of use addressing the foregoing.

SUMMARY

Disclosed herein is an endoscope imaging system having an endoscope configured to capture one or more images, the endoscope in communication with a laser system and a display, and a console in communication with the endoscope, the laser system and the display, the console configured to receive one or more parameter settings from the laser system, receive the one or more captured images from the endoscope, generate one or more icons corresponding to the parameter settings, and overlay the icons on the captured images depicted on the display.

In some embodiments, the console is coupled with the endoscope via a wired connection.

In some embodiments, the one or more of the laser system, the endoscope, or the display are coupled I with the console via a wireless connection.

In some embodiment, the console includes one or more processors, an energy source, non-transitory computer readable medium and a plurality of logic modules.

In some embodiments, the plurality of logic modules are configured to do one or more of receiving one or more parameter settings from the laser system, receiving one or more captured images from the endoscope, selecting the one or more parameter settings to depict on the display, generating one or more icons corresponding to the one or more parameter settings, overlaying the one or more icons on the one or more captured images, and depicting the one or more icons overlaid on the one or more captured images on the display.

In some embodiments, the parameter settings include one or more of a pulse energy, a pulse frequency, a pulse duration, a total power, and a pulse width.

In some embodiments, the console is included within an image overlay unit.

In some embodiments, the image overlay unit includes a control panel having a plurality of selection buttons and a directional button, where each selection button corresponds to one parameter setting, and where the directional button is configured to move the one or more icons around the display screen.

In some embodiments, the image overlay unit is wired to each of the endoscope, the laser system, and the display.

In some embodiments, the image overlay unit includes a laser system input, an endoscope input, and a display output.

Also disclosed herein is a method of depicting parameter settings of a laser system on a display of an endoscope including configuring one or more parameter settings of the laser system, capturing one or more images using the endoscope, generating one or more icons using a console. where the console is in communication with the laser system, the endoscope, and the display. The method further includes overlaying the one or more icons on the captured images, and depicting the icons together with the captured images on the display.

In some embodiments, one or more of the laser system, the endoscope, or the display are coupled with the console via a wired connection.

In some embodiments, one or more of the laser system, the endoscope, or the display are coupled with the console via a wireless connection.

In some embodiments, the console is included within an image overlay unit.

In some embodiments, the parameter settings include one or more of a pulse energy, a pulse frequency, a pulse duration, a total power, and a pulse width.

In some embodiments, generating one or more icons includes a user selecting the one or more parameter settings to be depicted on the display.

In some embodiments, the one or more icons correspond to the one or more parameter settings.

In some embodiments, the one or more icons includes icons for all of the parameter settings received by the console.

In some embodiments, the one or more icons includes icons for the parameter settings selected by the user to be depicted on the display.

In some embodiments, overlaying the one or more icons on the captured images includes (i) receiving the one or more parameter settings from the laser system by the console and (ii) receiving the one or more captured images from the endoscope by the console.

In some embodiments, depicting the icons and the captured images on the display includes the user determining the icons to be depicted on the display.

In some embodiments, the user selecting the one or more parameter settings to be depicted on the display using a control panel of an image overlay unit.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
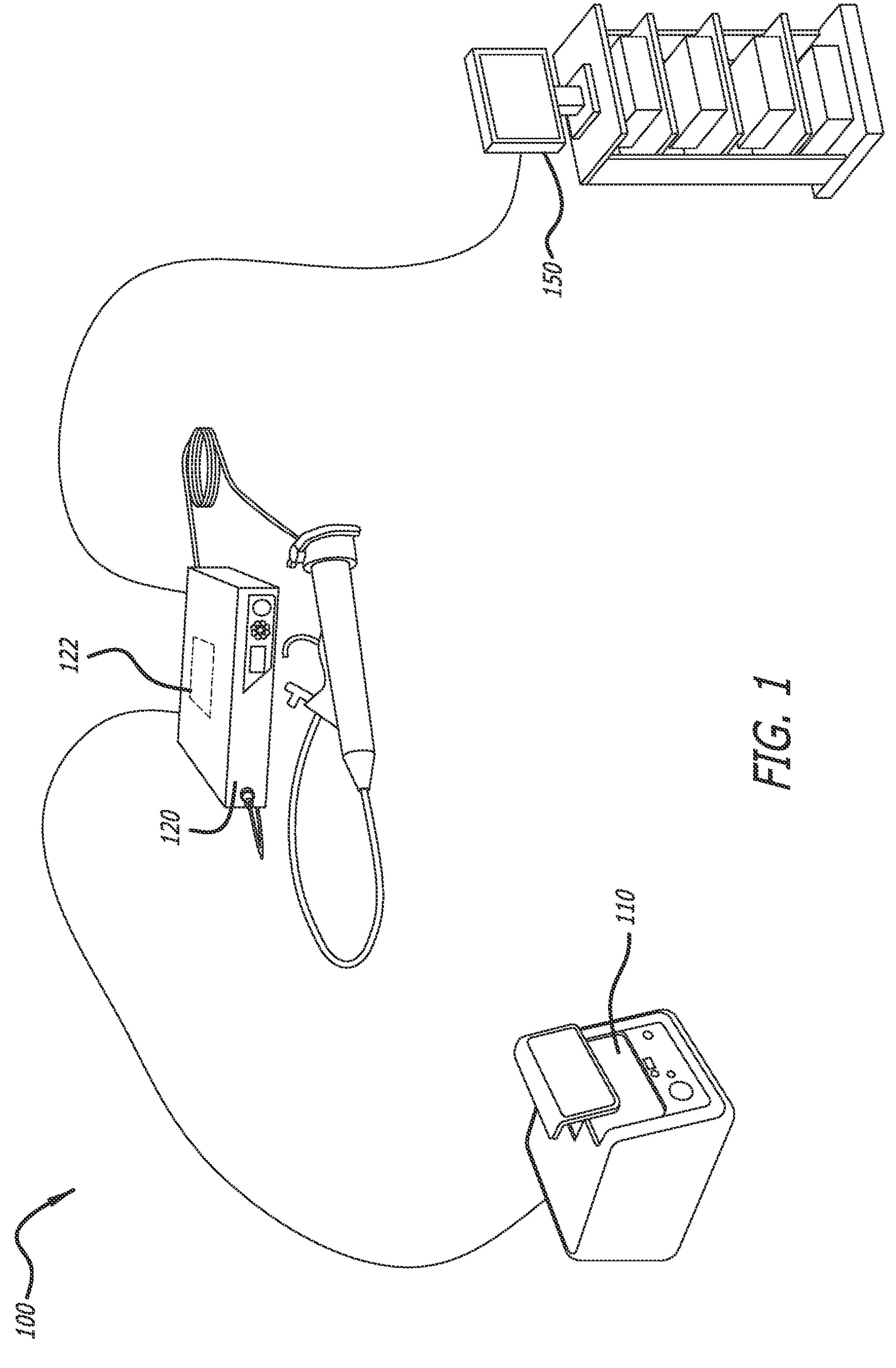
FIG. 1 illustrates a perspective view of an endoscope imaging system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC," etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

FIG. 1 illustrates a perspective view of an endoscope imaging system 100, in accordance with some embodiments. In some embodiments, the endoscope imaging system 100 includes a laser system 110, an endoscope 120 and a display 150. The endoscope 120 may be in communication with each of the laser system 110 and the display 150. In some embodiments, the endoscope 120 may be wired to the laser system 110 and the display 150 or in wireless communication with at least one of the laser system 110 and the display 150. During use, the endoscope 120 may be configured to capture one or more images from a patient while the laser system 110 is also in use on the patient. In some embodiments, the captured images may include live images. In some embodiments, the endoscope 120 includes a console 122 in communication with each of the laser system 110, the endoscope 120 and the display 150, the console 122 configured to receive one or more parameter settings from the laser system 110, overlay one or more icons depicting the one or more parameter settings on the captured images from the endoscope 120 and depict the captured endoscope image and the icons of the parameter setting on the display 150. Advantageously, the laser system 110 may be placed anywhere in an operating room while allowing a clinician to monitor progress of the endoscope 120 and verify the one or more parameter settings of the laser system 110 on the display 150. In some embodiments, the endoscope 120 may include an ureteroscope.

Figure 2:
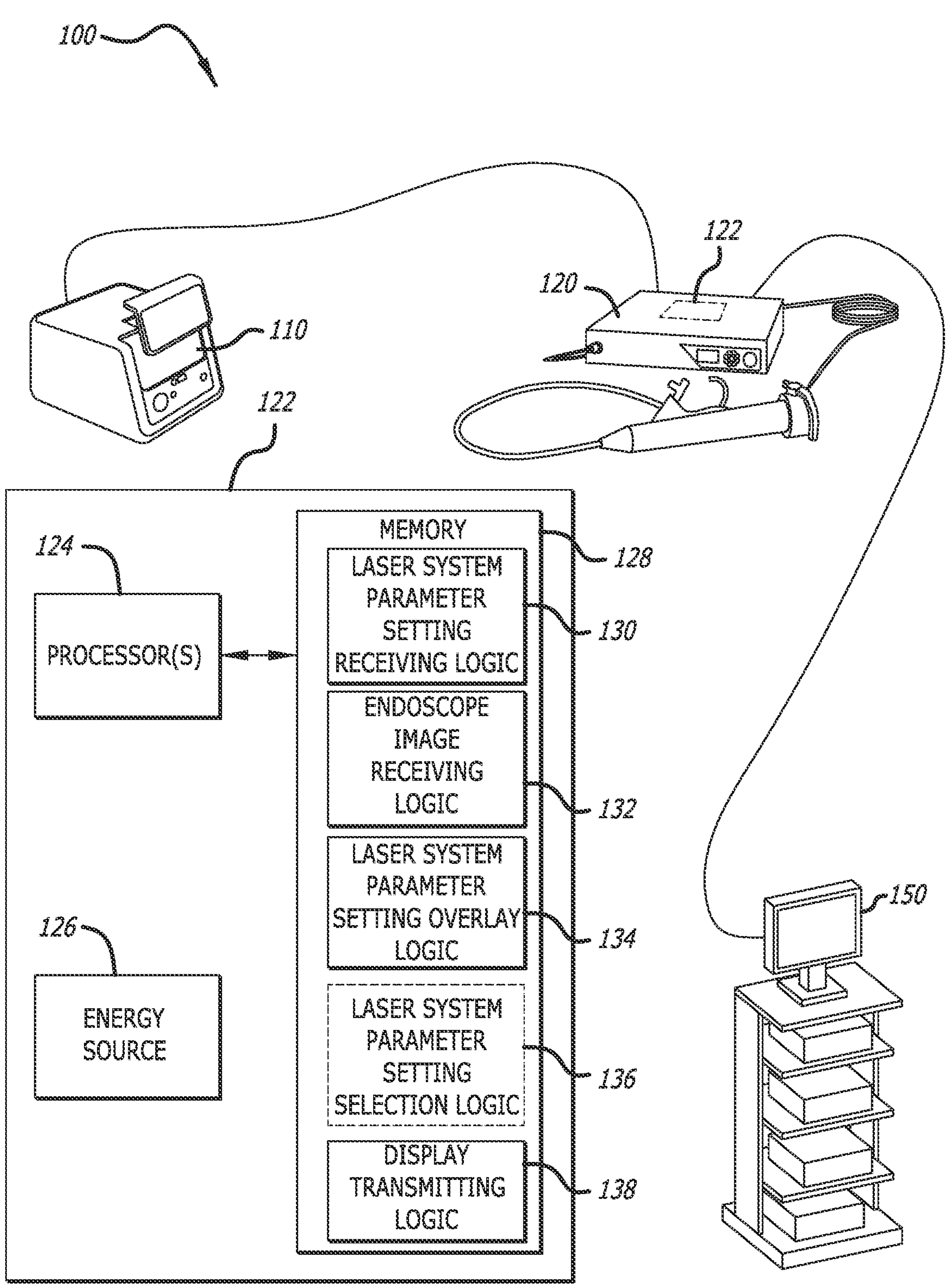
FIG. 2 illustrates a block diagram of some components of the endoscope imaging system, in accordance with some embodiments.

FIG. 2 illustrates a block diagram of some components of the endoscope imaging system 100, in accordance with some embodiments. In some embodiments, the endoscope 120 may include the console 122 having one or more processors 124, an energy source 126, non-transitory computer readable medium ("memory") 128 and a plurality of logic modules. In some embodiments, the console 122 is wired to or in wireless communication with the laser system 110, the endoscope 120 and the display 150. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like. In some embodiments, the console 122 may be coupled to the endoscope 120, integrated into the endoscope 120 or may be a stand-alone unit, as further described below. In some embodiments, the energy source 126 may include a battery or a power supply, including the power supply of the endoscope 120.

In some embodiments, the plurality of logic modules may include a laser system parameter setting receiving logic 130, an endoscope image receiving logic 132, a laser system parameter setting overlay logic 134, laser system parameter setting selection logic 136 and a display transmitting logic 138. In some embodiments, the laser system parameter setting receiving logic 130 may be configured to receive the one or more parameter settings from the laser system 110. In some embodiments, the one or more parameters may include one or more of: pulse energy (Joules), pulse frequency (Hertz), pulse duration (microseconds), total power (Watts), or pulse width. In some embodiments, the endoscope image receiving logic 132 may be configured to receive the one or more captured images from the endoscope 120. In some embodiments, the captured images may include live images. In some embodiments, the laser system parameter setting overlay logic 134 may be configured to generate and overlay on the captured endoscope image, one or more icons depicting the one or more parameter settings received from the laser system 110. In some embodiments, the icons may include shapes, text, numbers or a combination thereof, including the name of the parameter setting, the numerical value of the parameter setting, and the unit of measure of the parameter setting. In some embodiments, the laser system parameter setting selection logic 136 may be configured to allow a user to select/determine which of the one or more parameter settings received from the laser system 110 are overlaid on the endoscope images. In some embodiments, all of the parameter settings received from the laser system 110 may be depicted on the display 150. In some embodiments, the laser system parameter setting overlay logic 134 may be configured to generate icons for all of the parameter settings received from the laser system 110 and overlay only the parameter settings determined/selected by the user. In some embodiments, the laser system parameter setting overlay logic 134 may be configured to generate icons for only the parameter settings determined by the user through the laser system parameter setting selection logic 136. In some embodiments, the display transmitting logic 138 may be configured to transmit the captured image with the overlaid icons depicting the one or more parameter settings on the display 150.

Figure 3A:
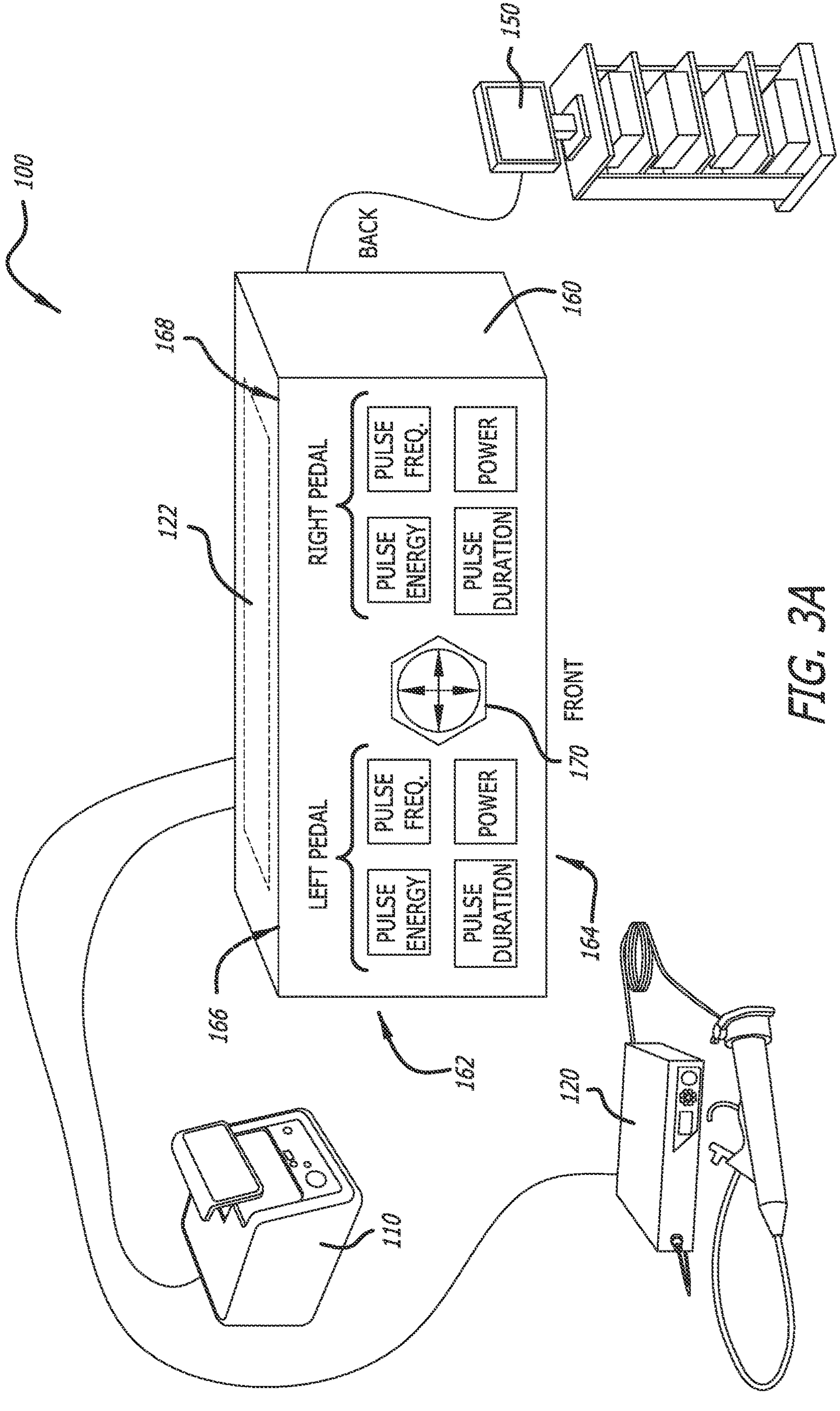
FIG. 3A illustrates a perspective view of the endoscope imaging system including an image overlay unit, in accordance with some embodiments.

FIG. 3A illustrates a perspective view of the endoscope imaging system 100 including an image overlay unit 160, in accordance with some embodiments. In some embodiments, the console 122 may be included in a stand-alone image overlay unit 160 that may be in communication with each of the laser system 110, the endoscope 120 and the display 150, the image overlay unit 160 may be configured to receive the parameter settings from the laser system 110 and the one or more images captured from the endoscope 120. Advantageously, the stand-alone image overlay unit 160 may be configured to receive captured image input from an endoscope from any manufacturer that includes a standard video output on the endoscope. Furthermore, the image overlay unit 160 may be placed anywhere in a procedure room including near the display 150, allowing the user to focus on the procedure. The image overlay unit 160 may be configured to overlay one or more icons of one or more parameter settings from the laser system 110 atop the captured images depicted on the display 150 as described above. In some embodiments, the image overlay unit 160 may include a control panel 162, located on the front of the image overlay unit 160. The control panel 162 may be configured to allow a user to control which parameter settings of the laser system 150 are depicted on the display 150. In some embodiments, the control panel 162 may be configured to have one or more selection buttons 164, wherein each selection button corresponds to a parameter setting of the laser system 110 that may be depicted on the display 150. In an embodiment, the selection buttons 164 may be organized or grouped into two sections, a left pedal section 166, corresponding to a left pedal on a laser system control pedal module (not shown) and a right pedal section 168, corresponding to a right pedal on a laser system control pedal module. The user may select the parameter setting to be depicted on the display 150 by selecting the button 164 corresponding to the parameter setting the user desires. In this embodiment, the image overlay unit 160 may include a directional button 170 configured to move the one or more of the depicted icons around the display screen 150. In some embodiments, the laser system 110, the endoscope 120 and the display 150 may be coupled to the back side of the image overlay unit 160.

Figure 3B:
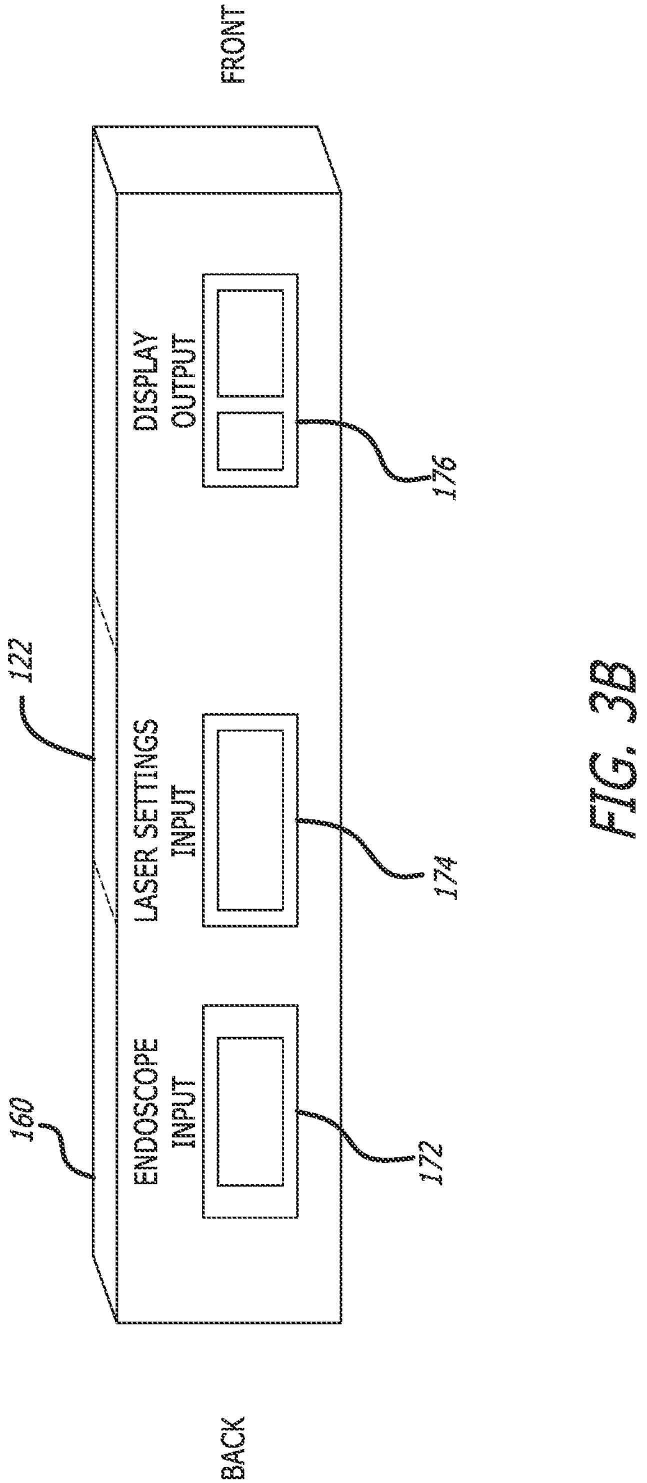
FIG. 3B illustrates a back view of the image overlay unit, in accordance with some embodiments.

FIG. 3B illustrates a back view of the image overlay unit 160, in accordance with some embodiments. The back side of the image overlay unit 160 may include a laser system input 174, an endoscope input 172 and a display output 176. In some embodiments, the laser system input 174 may include any number of standard inputs (e.g., Ethernet, component video, composite audio/video, VGA, Fire Wire, Serial Port, DVI, HDMI, Parallel Port, USB Type-C, USB Port, Optical Audio Toslink or the like). In some embodiments, the endoscope input 172 may include a standard video input (e.g., HDMI, mini HDMI, micro HDMI, VGA, mini VGA, DVI-D, DVI-I, mini DVI, micro DVI, DisplayPort, mini DisplayPort, USB Type-C, Thunderbolt, or the like) to be received from the endoscope 120. In some embodiments, the display output 176 may include a standard video output (e.g., HDMI, mini HDMI, micro HDMI, VGA, mini VGA, DVI-D, DVI-I, mini DVI, micro DVI, DisplayPort, mini DisplayPort, USB Type-C, Thunderbolt, or the like).

Figure 4:
FIG. 4 illustrates a depiction of a captured image by the endoscope displaying the icons of the parameter settings of the laser system on the display, in accordance with some embodiments.

FIG. 4 illustrates a depiction of a captured image by the endoscope 120 displaying the icons of the parameter settings of the laser system 110 on the display 150, in accordance with some embodiments. In some embodiments, the one or more icons 180 may be depicted near a corner or near a side of the display 150 so as to not obstruct the captured image. In some embodiments, wherein the laser system 110 includes two pedals, the one or more icons 180 may be distinguished by location on the display 150. For example, as illustrated in FIG. 4, the icons 180A corresponding to the parameter settings for the left pedal of the laser system 110 are located on the top left side of the display 150 and the icons 180B corresponding to the parameter settings for the top right pedal of the laser system 110 are located on the right side of the display 150. In some embodiments, the directional button 170 may be configured to move the one or more icons 180 to various locations on the display screen at a user's discretion.

Figure 5:
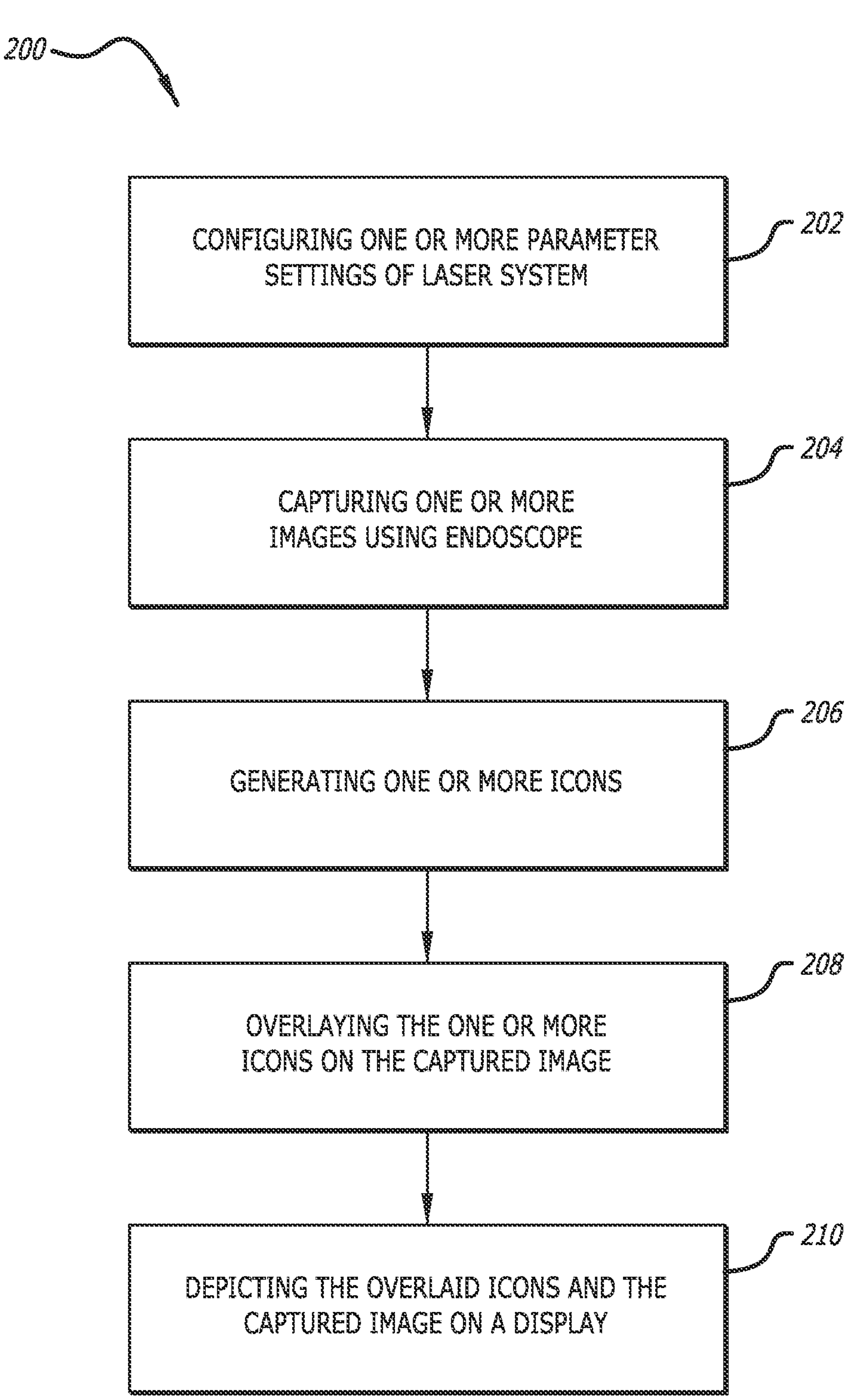
FIG. 5 illustrates a flow chart of an exemplary method of displaying parameter settings of the laser system on the display of an endoscope, in accordance with some embodiments.

FIG. 5 illustrates a flow chart of an exemplary method 200 of displaying parameter settings of the laser system 110 on a display 150 of an endoscope 120, in accordance with some embodiments. The method 200 includes configuring one or more parameter settings of the laser system 110 (block 202). In some embodiments, the one or more parameter settings include one or more of a pulse energy, a pulse frequency, a pulse duration, a total power, and a pulse width. The method 200 further includes capturing one or more images using the endoscope 120 (block 204). The method 200 further includes generating one or more icons 180 (block 206). In some embodiments, generating one or more icons 180 includes the console 122 generating the one or more icons 180. In some embodiments, the console 122 is included within the image overlay unit 160. In some embodiments, the icons 180 may include shapes and/or text that correspond to the one or more parameter settings of the laser system 110. In some embodiments, generating one or more icons 180 includes a user selecting the one or more parameter settings to be depicted on the display 150. In some embodiments, generating one or more icons 180 includes the console 122 generating the one or more icons 180 for the all the parameter settings received by the console 122 or includes the console 122 generating the one or more icons 180 for only the parameter settings selected by the user to be depicted on the display 150.

The method 200 further includes overlaying the one or more icons 180 on the captured image (block 208). In some embodiments, overlaying the one or more icons 180 on the captured images includes the console 122 (i) receiving the one or more parameter settings from the laser system 110 and (ii) receiving the one or more captured images from the endoscope 120. In some embodiments, overlaying includes overlaying the one or more icons 180 on the live captured image. The method 200 further includes depicting the overlaid icons 180 and the captured image on the display 150 (block 210). In some embodiments, depicting the icons 180 and the captured images on the display 150 includes the user determining the icons 180 depicted on the display 150. In some embodiments, the user determining the icons 180 depicted on the display 150 includes the user using the control panel 162 of an image overlay unit 160 to select the one or more parameter settings to be depicted on the display 150. In some embodiments, depicting the overlaid icons 180 and the captured image on the display 150 includes depicting the icons 180 towards the sides or the corners of the display 150.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An endoscope imaging system, comprising:

an endoscope configured to capture one or more images, the endoscope in communication with a laser system and a display; and a console in communication with the endoscope, the laser system, and the display, the console configured to:

receive one or more parameter settings from the laser system, receive the one or more images from the endoscope, generate one or more icons corresponding to the one or more parameter settings, and overlay the one or more icons on the one or more images depicted on the display, wherein the console is included within an image overlay unit, the image overlay unit including a control panel having a plurality of selection buttons and a direction button, and wherein each selection button corresponds to one parameter setting and the direction button is configured to move the one or more icons around the display.

2. The endoscope imaging system according to claim 1, wherein the console is wired to the endoscope.

3. The endoscope imaging system according to claim 1, wherein the console is in wireless communication with one or more of the laser system, the endoscope, or the display.

4. The endoscope imaging system according to claim 1, wherein the console includes one or more processors, an energy source, a non-transitory computer readable medium, and a plurality of logic modules.

5. The endoscope imaging system according to claim 4, wherein the plurality of logic modules are configured to perform operations, comprising:

receiving the one or more parameter settings from the laser system;

receiving one or more images from the endoscope;

selecting the one or more parameter settings to depict on the display;

generating the one or more icons corresponding to the one or more parameter settings;

overlaying the one or more icons atop the one or more images; and depicting the one or more icons overlaid on the one or more captured images on the display.

6. The endoscope imaging system according to claim 1, wherein the one or more parameter settings include one or more of a pulse energy, a pulse frequency, a pulse duration, a total power, or a pulse width.

7. The endoscope imaging system according to claim 1, wherein the image overlay unit is coupled with each of the endoscope, the laser system, and the display via wired connection.

8. The endoscope imaging system according to claim 7, wherein the image overlay unit includes a laser system input, an endoscope input, and a display output.

9. A method of depicting parameter settings of a laser system on a display of an endoscope, comprising:

configuring one or more parameter settings of the laser system;

capturing one or more images using the endoscope;

generating one or more icons using a console in communication with the laser system, the endoscope, and the display, wherein the console is included within an image overlay unit, the image overlay unit including a control panel having a plurality of selection buttons and a direction button, and wherein each selection button corresponds to one parameter setting and the directional button is configured to move the one or more icons around the display;

overlaying the one or more icons atop the one or more images; and depicting the one or more icons and the one or more images on the display.

10. The method according to claim 9, wherein one or more of the laser system, the endoscope, or the display are coupled with the console via a wired connection.

11. The method according to claim 9, wherein one or more of the laser system, the endoscope, or the display are coupled with the console via a wireless connection.

12. The method according to claim 9, wherein the parameter settings include one or more of a pulse energy, a pulse frequency, a pulse duration, a total power, or a pulse width.

13. The method according to claim 9, wherein generating the one or more icons includes a user selecting the one or more parameter settings to be depicted on the display.

14. The method according to claim 13, wherein the one or more parameter settings to be depicted on the display are selected by the user via the control panel of the image overlay unit.

15. The method according to claim 9, wherein the one or more icons correspond to the one or more parameter settings.

16. The method according to claim 15, wherein the one or more icons includes icons for all of the parameter settings received by the console.

17. The method according to claim 15, wherein the one or more icons includes icons for the parameter settings selected by a user.

18. The method according to claim 9, wherein overlaying the one or more icons on the one or more images includes:

receiving the one or more parameter settings from the laser system by the console, and receiving the one or more images from the endoscope by the console.

19. The method according to claim 9, wherein depicting the one or more icons and the one or more images on the display includes a user determining the icons depicted on the display.

* * * * *